(12) United States Patent
Mizutani et al.

(10) Patent No.: US 7,119,253 B2
(45) Date of Patent: Oct. 10, 2006

(54) DNAS CODING FOR FLAVONE SYNTHASE, METHODS OF USING FLAVONE SYNTHASE DNAS, AND PLANTS, FLOWERS, AND VECTORS CONTAINING FLAVONE SYNTHASE DNAS

(75) Inventors: Masako Mizutani, Kyoto (JP); Yoshikazu Tanaka, Otsu (JP); Takaaki Kusumi, Suita (JP); Shin-ichi Ayabe, Yamato (JP); Tomoyoshi Akashi, Yamato (JP)

(73) Assignees: Suntory Flowers Limited, Tokyo (JP); Suntory Limited, Osaka (JP)

( * ) Notice: Subject to any disclaimer, the term of this patent is extended or adjusted under 35 U.S.C. 154(b) by 314 days.

(21) Appl. No.: 10/411,225

(22) Filed: Apr. 11, 2003

(65) Prior Publication Data

US 2004/0261146 A1    Dec. 23, 2004

Related U.S. Application Data

(60) Division of application No. 09/672,785, filed on Sep. 29, 2000, now Pat. No. 6,596,927, which is a continuation of application No. PCT/JP00/04379, filed on Jun. 30, 2000, and a continuation of application No. PCT/JP00/00490, filed on Jan. 28, 1999.

(30) Foreign Application Priority Data

Jan. 29, 1999  (JP)  ................................. 11-22427
Jul. 19, 1999  (JP)  ................................. 11-205229

(51) Int. Cl.
  *A01H 5/00*   (2006.01)
  *C12N 15/29*  (2006.01)
  *C12N 15/82*  (2006.01)

(52) U.S. Cl. ................... 800/282; 800/298; 435/320.1; 536/23.6

(58) Field of Classification Search ............. 435/320.1; 536/23.2, 23.6; 800/282, 285, 298
See application file for complete search history.

(56) References Cited

FOREIGN PATENT DOCUMENTS

WO    WO 00/65073 A2    11/2000

OTHER PUBLICATIONS

Akashi et al., "Molecular Cloning and Biochemical Characterization of a Novel Cytochrome P450, Flavone Synthase II, that Catalyzes Direct Conversion of Flavanones to Flavones", *Plant Cell Physiology*, 40 (11):1182-86 (1999).
Akashi et al., "Identification of a cytochrome P450 cDNA encoding (2S)-flavanone 2-hydroxylase of licorice (*Glycyrrhiza echinata* L.; Fabaceae) which represents licodione synthase and flavone synthase II", *FEBS Letters* 431: 287-90 (1998).
Martens et al., "Genetic Control of Flavone Synthase II Activity in Flowers of *Gerbera* hydbrids", *Phytochemistry*, 49(7): 1953 58 (1998).
Akashi et al., "CYP81E1, a cytochrome P450 cDNA of licorice (*Glycyrrhiza echinata* L.), encodes isoflavone 2'-hydroxylase", *Biochemical and Biophysical Research Communications*, 251: 67-70 (1998).
Nakamura et al., "Induction of Isoflavonoid and Retrochalcone Branches of the Flavonoid Pathway in Cultured *Glycyrrhiza echinata* cells Treated with Yeast Extract", *Bioscience, Biotechnology and Biochemistry*, 63(9): 1618-1620 (1999).
Martens et al., "Cloning and expression of flavone synthase II from Gerbera hybrids," *The Plant Journal*, vol. 20, No. 5, pp. 611-618, 1999.
Siminszky et al., "Expression of a soybean cytochrome P450 monooxygenase cDNA in yeast and tobacco . . . ," *Plant Biology*, vol. 96, pp. 1750-1755, Feb. 1999.
Akashi et al., Direct Submission, Accession No. AB028152.
Fourgoux-Nicol et al, 1999, *Plant Molecular Biology*, 40:857:872.
Schopfer and Ebel, 1998, *Mol. Gen. Genet.*, 258:315-322.
Database EMBL [Online] Elsevier Science Publishers, Amsterdam, NL; Accession No.: AF156976, Jun. 21, 1999.
Database EMBL [Online] Accession No.: AB001380, Sep. 23, 1997.
Schopfer et al., "G. max mRNA for putative cytochrome P450, clone CP5- Identification of elicitor-induced cytochrome P450s of soybean (Glycine max L.) using differential display of MRNA," EMBL:GMC450CP5, 1997, (Abstract Only—XP002305184).
Akashi et al., "Cloning and Functional Expression of a Cytochrome P450 cDNA Encoding 2-Hydroxyisoflavanone Synthase Involved in Biosynthesis of the Isoflavonoid Skeleton in Licorice," *Plant Physiology*, 1999, vol. 121, pp. 821-828, American Society of Plant Physiologists, Lancaster, PA, USA.
Didier Mbeguie-A-Mbeguie, Rose-Marie Gomez, and Bernard Fils-Lycaon Molecular Cloning and Nucleotide Sequence of a Metallothionein-like Protein From Apricot Fruit (Accession No. U97494). Gene Expression During Fruit Ripening. (PGR97-160). Plant Physiol. 115: 1288.
Didier Mbeguie-A-Mbeguie, Rose-Marie Gomez, and Bernard Fils-Lycaon Molecular Cloning and Nucleotide Sequence of a Protein From Apricot Fruit (Accession No. U82760) Homologous to LEC14B Protein Isolated From *Lithospermum*. Gene Expression During Fruit Ripening. (PGR97-161). Plant Physiol. 115: 1288.
Ping Jin, Jun Sun, Rachel Nechushtai, Parag R. Chitnis Molecular Cloning Of The Psad Gene For The 16-Kda Subunit Of Photosystem I From The Thermophilic Cyanobacterium *Mastigocladus laminosus* (Accession No. U97518) (PGR97-162). Plant Physiol. 115: 1288.

(Continued)

*Primary Examiner*—David H Kruse
(74) *Attorney, Agent, or Firm*—Drinker Biddle & Reath LLP

(57) ABSTRACT

A DNA encoding a flavone synthase that synthesizes flavones from flavanones, vectors containing said DNAs, and plants expressing same are disclosed. Methods of producing the protein which synthesizes flavones from flavanones, methods of altering the composition of flavonoids or the amount of flavonoids in a plant, methods of altering flower color and plant photosensitivity, and methods of controlling interactions between plants expressing the protein and microorganisms are also disclosed.

21 Claims, 1 Drawing Sheet

OTHER PUBLICATIONS

U.T. Mukatira, U.S. Muchhal and K.G. Raghothama Cloning of *Arabidopsis thaliana* phosphate transporter gene, AtPT2 (Accession No. AF022872). (PGR97-163) Plant Physiol. 115: 1288.

Joshua C. Corrette-Bennett and Donald R. Straus Nucleotide Sequence of a cDNA Encoding *Volvax carteri* Acetolactate Synthase (Accession No. AF024632) (PGR97-164). Plant Physiol. 115: 1288.

Roel Peter Funke, Joy Lynn Kovar and Donald Paul Weeks Nucleotide Sequence of a cDNA Encoding *Chlamydomonas reinhardtii* Acetolactate Synthase (Accession No. AF022816) (PGR97-165). Plant Physiol. 115: 1288.

Didier Mbeguie-A-Mbegule, Rose-Marie Gomez, and Bernard Fils-Lycaon Molecular Cloning and Nucleotide Sequence of an Abscisic Acid-, Stress-, Ripening-Induced (ASR) -Like Protein From Apricot Fruit (Accession No. U93164). Gene Expression During Fruit Ripening. (PGR97-166). Plant Physiol. 115: 1288.

Tomoyoshi Akashi, Toshio Aoki, Nanako Kameya, Ikuo Nakamura, Shin-ichi Ayabe Two New Cytochrome P450 cDNAs (Accession Nos. AB001379 and AB001380) from Elicitor-Induced Licorice (*Glycyrrhiza echinata* L.) Cells (PGR97-167). Plant Physiol. 115: 1288.

Nicole Happel, David G. Robinson, Susanne E. H. Holstein An *Arabidopsis thaliana* cDNA Clone (Accession No. AF009631) is Homologous to the Micro-adaptins of Clathrin Coated Vesicle Adaptor Complexes. (PGR97-168). Plant Physiol. 115: 1289.

Narciso Campos, Luisa Maria Lois and Albert Boronat Nucleotide Sequence Of A Rice cDNA Encoding A Transketolase-Like Protein Homologous To The Arabidopsis *CLA 1* Gene Product (Accession No. AF024512) (PGR97-169). Plant Physiol. 115: 1289.

X. Z. He and R. A. Dixon A cDNA of an Additional Member of the Isoflavone-O-Methyltransferase (IOMT2) Gene Family in *Medicago sailva* (Accession No. AF023481) (PGR97-170). Plant Physiol. 115: 1289.

Plant Physiol., 115, 1288-1289 (1997).

SEQUENCE LISTING

<160> NUMBER OF SEQ ID NOS: 8

<210> SEQ ID NO 1
<211> LENGTH: 1724
<212> TYPE: DNA
<213> ORGANISM: Antirrhinum majus
<220> FEATURE:
<223> OTHER INFORMATION: Nucleotide sequence encoding a protein having
      an activity to directly convert flavanone to flavone

<400> SEQUENCE: 1
gctttacaca cacacacaca cacacacaca caaacaaaa atg tct aca ctt gtc     54
                                           Met Ser Thr Leu Val -continued

```
                                   1               5
tac agc aca ctc ttc atc ctc tca acc ctc ctc ctc acc ctc cta acc     102
Tyr Ser Thr Leu Phe Ile Leu Ser Thr Leu Leu Leu Thr Leu Leu Thr
                    10              15                  20 cgc acc cgc cgc aag acc cgc ccg ccc ggc cca tta gcc ctc ccc tta     150
Arg Thr Arg Arg Lys Thr Arg Pro Pro Gly Pro Leu Ala Leu Pro Leu
                25              30                  35 ata ggc cac tta cac ctc ctc ggc cca aag ctc cac cac acc ttc cac     198
Ile Gly His Leu His Leu Leu Gly Pro Lys Leu His His Thr Phe His
            40                  45                  50 caa ttc tcc caa cgc tac ggc ccg ctc atc cag ctc tac ctc ggc tcc     246
Gln Phe Ser Gln Arg Tyr Gly Pro Leu Ile Gln Leu Tyr Leu Gly Ser
        55                  60                  65 gtc cca tgc gtc gtc gct tcc acg ccc gaa ctc gcc cgc gaa ttc ctc     294
Val Pro Cys Val Val Ala Ser Thr Pro Glu Leu Ala Arg Glu Phe Leu
    70                  75                  80                  85 aag acg cac gaa ctc gac ttc tcg tcc cgc aag cac tcc acc gcc atc     342
Lys Thr His Glu Leu Asp Phe Ser Ser Arg Lys His Ser Thr Ala Ile
                    90                  95                  100 gac atc gtc acg tac gac tcc tcg ttc gcc ttc gcg ccg tac ggg ccg     390
Asp Ile Val Thr Tyr Asp Ser Ser Phe Ala Phe Ala Pro Tyr Gly Pro
                105                 110                 115 tac tgg aaa ttc atc aag aaa tta tgt act tac gag cta ctg ggt gcc     438
Tyr Trp Lys Phe Ile Lys Lys Leu Cys Thr Tyr Glu Leu Leu Gly Ala
                120                 125                 130 cgg aac ttg agc cat ttc cag ccc att aga gct ttg gag gtc aac agt     486
Arg Asn Leu Ser His Phe Gln Pro Ile Arg Ala Leu Glu Val Asn Ser
135                 140                 145 ttc ttg aga att ttg tac gag aaa aca gag cag aaa cag agt gtt aat     534
Phe Leu Arg Ile Leu Tyr Glu Lys Thr Glu Gln Lys Gln Ser Val Asn
150                 155                 160                 165 gtg act gag gag ctt gtg aag ctg acg agt aat gtg atc agt aac atg     582
Val Thr Glu Glu Leu Val Lys Leu Thr Ser Asn Val Ile Ser Asn Met
                170                 175                 180 atg ttg ggg atc agg tgt tcg ggg acg gaa ggg gag gcg gag gtg gcg     630
Met Leu Gly Ile Arg Cys Ser Gly Thr Glu Gly Glu Ala Glu Val Ala
                185                 190                 195 agg acg gtg ata agg gag gtg acg cag ata ttt ggg gag ttt gat gtg     678
Arg Thr Val Ile Arg Glu Val Thr Gln Ile Phe Gly Glu Phe Asp Val
                200                 205                 210 tcg gag att gtt tgg ttt tgt aag aat ttg gat ctg cag ggg att agg     726
Ser Glu Ile Val Trp Phe Cys Lys Asn Leu Asp Leu Gln Gly Ile Arg
        215                 220                 225 aag agg tcg gag gat att agg agg agg tat gat gct ttg ttg gag aag     774
Lys Arg Ser Glu Asp Ile Arg Arg Arg Tyr Asp Ala Leu Leu Glu Lys
230                 235                 240                 245 att att agt gat agg gag agg ttg agg ttg agg ggg ggt ggt ggt gga     822
Ile Ile Ser Asp Arg Glu Arg Leu Arg Leu Arg Gly Gly Gly Gly Gly
                250                 255                 260 ggg ggt gga gag gtg aag gat ttt ttg gat atg ttg ttg gat gtg atg     870
Gly Gly Gly Glu Val Lys Asp Phe Leu Asp Met Leu Leu Asp Val Met
            265                 270                 275 gag agt gag aaa tcg gag gtg gag ttt acg agg gag cat ctc aaa gct     918
Glu Ser Glu Lys Ser Glu Val Glu Phe Thr Arg Glu His Leu Lys Ala
                280                 285                 290 ttg att ctg gat ttc ttc act gcc ggt aca gac aca aca gca atc aca     966
Leu Ile Leu Asp Phe Phe Thr Ala Gly Thr Asp Thr Thr Ala Ile Thr
            295                 300                 305 aca gaa tgg gca ata gca gaa ctc att agc aat cca aat gta ctc aaa    1014
```

```
                                                  1062
aaa gct caa gaa gag atg gac aaa gtc ata gga tca caa agg ttg ttg
Lys Ala Gln Glu Glu Met Asp Lys Val Ile Gly Ser Gln Arg Leu Leu
            330                 335                 340

1110
caa gaa tcc gac gcc cct aac ttg cct tac ctc aac gcg atc ata aaa
Gln Glu Ser Asp Ala Pro Asn Leu Pro Tyr Leu Asn Ala Ile Ile Lys
        345                 350                 355

1158
gaa acg ttc cgt ctc cac cct cca atc ccc atg ctc act aga aaa tca
Glu Thr Phe Arg Leu His Pro Pro Ile Pro Met Leu Thr Arg Lys Ser
    360                 365                 370

1206
att tct gac gtt gtg gtc aac ggg tac acg atc cct gcc aaa acg cta
Ile Ser Asp Val Val Val Asn Gly Tyr Thr Ile Pro Ala Lys Thr Leu
375                 380                 385

1254
ttg ttt gtc aac ctt tgg tcc atg gga agg aat cct aac tac tgg gaa
Leu Phe Val Asn Leu Trp Ser Met Gly Arg Asn Pro Asn Tyr Trp Glu
390                 395                 400                 405

1302
aat ccg atg gag ttc cga ccc gag agg ttt ctc gag aaa ggg acc ggg
Asn Pro Met Glu Phe Arg Pro Glu Arg Phe Leu Glu Lys Gly Thr Gly
            410                 415                 420

1350
tcg ata gac gtt aaa ggg cag cat ttc gag ttg ctg ccg ttt ggc acg
Ser Ile Asp Val Lys Gly Gln His Phe Glu Leu Leu Pro Phe Gly Thr
        425                 430                 435

1398
ggc agg cgg ggc tgc ccg ggg atg ttg tta ggc atg cag gag ttg ttt
Gly Arg Arg Gly Cys Pro Gly Met Leu Leu Gly Met Gln Glu Leu Phe
    440                 445                 450

1446
agt att atc ggg gct atg gtg cag tgc ttc gat tgg aaa ctg ccc gat
Ser Ile Ile Gly Ala Met Val Gln Cys Phe Asp Trp Lys Leu Pro Asp
455                 460                 465

1494
ggt gtg aag tcg gtc gac atg acc gag cgg ccc ggg ttg acg gct cca
Gly Val Lys Ser Val Asp Met Thr Glu Arg Pro Gly Leu Thr Ala Pro
470                 475                 480                 485

1542
cgt gcc aat gat ttg gtg tgc caa ttg gtg cca cgg att gac ccg gtc
Arg Ala Asn Asp Leu Val Cys Gln Leu Val Pro Arg Ile Asp Pro Val
            490                 495                 500

1592
gtt gtc tcc gga ccg tgaaccttaa ggtagtatcg ataatctgtt taatt
Val Val Ser Gly Pro
            505 aaattgttat tgttgtgag gatttgattt ttgttatgta tgattatgcg tggattaaga    1652 taagcctgca aggacaaatt ccctttcttt gattgatgtc aatgagtttg tgtcaaaaaa    1712 aaaaaaaaaa aa                                                        1724

<210> SEQ ID NO 2
<211> LENGTH: 506
<212> TYPE: PRT
<213> ORGANISM: Antirrhinum majus
<220> FEATURE:
<223> OTHER INFORMATION: Amino acid sequence of a protein having
      an activity to directly convert flavanone to flavone

<400> SEQUENCE: 2

Met Ser Thr Leu Val Tyr Ser Thr Leu Phe Ile Leu Ser Thr Leu Leu
1               5                   10                  15

Leu Thr Leu Leu Thr Arg Thr Arg Arg Lys Thr Arg Pro Pro Gly Pro
            20                  25                  30

Leu Ala Leu Pro Leu Ile Gly His Leu His Leu Gly Pro Lys Leu
        35                  40                  45

His His Thr Phe His Gln Phe Ser Gln Arg Tyr Gly Pro Leu Ile Gln
    50                  55                  60
```

-continued

```
Leu Tyr Leu Gly Ser Val Pro Cys Val Val Ala Ser Thr Pro Glu Leu
 65                  70                  75                  80

Ala Arg Glu Phe Leu Lys Thr His Glu Leu Asp Phe Ser Ser Arg Lys
                 85                  90                  95

His Ser Thr Ala Ile Asp Ile Val Thr Tyr Asp Ser Ser Phe Ala Phe
            100                 105                 110

Ala Pro Tyr Gly Pro Tyr Trp Lys Phe Ile Lys Lys Leu Cys Thr Tyr
        115                 120                 125

Glu Leu Leu Gly Ala Arg Asn Leu Ser His Phe Gln Pro Ile Arg Ala
    130                 135                 140

Leu Glu Val Asn Ser Phe Leu Arg Ile Leu Tyr Glu Lys Thr Glu Gln
145                 150                 155                 160

Lys Gln Ser Val Asn Val Thr Glu Glu Leu Val Lys Leu Thr Ser Asn
                165                 170                 175

Val Ile Ser Asn Met Met Leu Gly Ile Arg Cys Ser Gly Thr Glu Gly
            180                 185                 190

Glu Ala Glu Val Ala Arg Thr Val Ile Arg Glu Val Thr Gln Ile Phe
        195                 200                 205

Gly Glu Phe Asp Val Ser Glu Ile Val Trp Phe Cys Lys Asn Leu Asp
    210                 215                 220

Leu Gln Gly Ile Arg Lys Arg Ser Glu Asp Ile Arg Arg Arg Tyr Asp
225                 230                 235                 240

Ala Leu Leu Glu Lys Ile Ile Ser Asp Arg Glu Arg Leu Arg Leu Arg
                245                 250                 255

Gly Gly Gly Gly Gly Gly Gly Glu Val Lys Asp Phe Leu Asp Met
            260                 265                 270

Leu Leu Asp Val Met Glu Ser Glu Lys Ser Glu Val Glu Phe Thr Arg
        275                 280                 285

Glu His Leu Lys Ala Leu Ile Leu Asp Phe Phe Thr Ala Gly Thr Asp
    290                 295                 300

Thr Thr Ala Ile Thr Thr Glu Trp Ala Ile Ala Glu Leu Ile Ser Asn
305                 310                 315                 320

Pro Asn Val Leu Lys Lys Ala Gln Glu Glu Met Asp Lys Val Ile Gly
                325                 330                 335

Ser Gln Arg Leu Leu Gln Glu Ser Asp Ala Pro Asn Leu Pro Tyr Leu
            340                 345                 350

Asn Ala Ile Ile Lys Glu Thr Phe Arg Leu His Pro Pro Ile Pro Met
        355                 360                 365

Leu Thr Arg Lys Ser Ile Ser Asp Val Val Asn Gly Tyr Thr Ile
    370                 375                 380

Pro Ala Lys Thr Leu Leu Phe Val Asn Leu Trp Ser Met Gly Arg Asn
385                 390                 395                 400

Pro Asn Tyr Trp Glu Asn Pro Met Glu Phe Arg Pro Glu Arg Phe Leu
                405                 410                 415

Glu Lys Gly Thr Gly Ser Ile Asp Val Lys Gly Gln His Phe Glu Leu
            420                 425                 430

Leu Pro Phe Gly Thr Gly Arg Arg Gly Cys Pro Gly Met Leu Leu Gly
        435                 440                 445

Met Gln Glu Leu Phe Ser Ile Ile Gly Ala Met Val Gln Cys Phe Asp
    450                 455                 460

Trp Lys Leu Pro Asp Gly Val Lys Ser Val Asp Met Thr Glu Arg Pro
465                 470                 475                 480
```

-continued

```
Gly Leu Thr Ala Pro Arg Ala Asn Asp Leu Val Cys Gln Leu Val Pro
                485                 490                 495

Arg Ile Asp Pro Val Val Ser Gly Pro
        500                 505
```

<210> SEQ ID NO 3
<211> LENGTH: 1730
<212> TYPE: DNA
<213> ORGANISM: Torenia hybrida
<220> FEATURE:
<223> OTHER INFORMATION: Nucleotide sequence encoding a protein having
      an activity to directly convert flavanone to flavone

<400> SEQUENCE: 3

```
atcgaaaccg ctatatcatt acatttacaa cagcgctaaa aaaatatata taaagc         56 atg gac aca gtc tta atc aca ctc tac acc gcc ctg ttc gtc atc acc     104
Met Asp Thr Val Leu Ile Thr Leu Tyr Thr Ala Leu Phe Val Ile Thr
  1               5                  10                  15 acc acc ttc ctc ctc ctc cgc cga agg gga cca ccg tct ccg ccc         152
Thr Thr Phe Leu Leu Leu Arg Arg Arg Gly Pro Pro Ser Pro Pro
                 20                  25                  30 ggt cct ctc tcc cta ccc ata att ggc cac ctc cac ctc ctc ggc cca     200
Gly Pro Leu Ser Leu Pro Ile Ile Gly His Leu His Leu Leu Gly Pro
             35                  40                  45 aga ctc cac cac acg ttc cat gaa ttc tca ctc aaa tac ggc cca ttg     248
Arg Leu His His Thr Phe His Glu Phe Ser Leu Lys Tyr Gly Pro Leu
     50                  55                  60 atc cag ctc aag ctc ggc tcg atc ccg tgc gtc gtg gcc tcg acg ccc     296
Ile Gln Leu Lys Leu Gly Ser Ile Pro Cys Val Val Ala Ser Thr Pro
 65                  70                  75                  80 gag ctc gcg aga gag ttt ctt aag acg aac gag ctc gcg ttc tcc tct     344
Glu Leu Ala Arg Glu Phe Leu Lys Thr Asn Glu Leu Ala Phe Ser Ser
                 85                  90                  95 cgc aag cac tct acg gcc ata gac atc gtc acc tac gac tcg tcc ttt     392
Arg Lys His Ser Thr Ala Ile Asp Ile Val Thr Tyr Asp Ser Ser Phe
                100                 105                 110 gct ttc tct ccg tac gga ccc tac tgg aag tac atc aag aaa ctg tgt     440
Ala Phe Ser Pro Tyr Gly Pro Tyr Trp Lys Tyr Ile Lys Lys Leu Cys
            115                 120                 125 acc tac gag ctg ctc gga gcg agg aac ctc gga cac ttt cag ccc att     488
Thr Tyr Glu Leu Leu Gly Ala Arg Asn Leu Gly His Phe Gln Pro Ile
        130                 135                 140 agg aat ctc gag gtc agg tcc ttt ctg cag ctt ctg atg cac aag agc     536
Arg Asn Leu Glu Val Arg Ser Phe Leu Gln Leu Leu Met His Lys Ser
145                 150                 155                 160 ttt aag ggc gag agt gtg aat gtg aca gac gag ctg gtg agg ctg acg     584
Phe Lys Gly Glu Ser Val Asn Val Thr Asp Glu Leu Val Arg Leu Thr
                165                 170                 175 agc aat gtg ata tcc cac atg atg ctg agc ata agg tgc tcg gaa gat     632
Ser Asn Val Ile Ser His Met Met Leu Ser Ile Arg Cys Ser Glu Asp
            180                 185                 190 gaa ggc gat gct gag gcg gcg aga aca gtg ata cgc gag gtg acg cag     680
Glu Gly Asp Ala Glu Ala Ala Arg Thr Val Ile Arg Glu Val Thr Gln
        195                 200                 205 ata ttt ggg gaa ttc gat gtt acg gac ata ata tgg ttt tgc aag aaa     728
Ile Phe Gly Glu Phe Asp Val Thr Asp Ile Ile Trp Phe Cys Lys Lys
    210                 215                 220 ttc gat ctg cag ggg ata aag aag agg tca gag gat att cag agg agg     776
Phe Asp Leu Gln Gly Ile Lys Lys Arg Ser Glu Asp Ile Gln Arg Arg
225                 230                 235                 240
```

| | | |
|---|---|---|
| tat gat gct ttg ctc gag aag att att agt gat aga gag aga tcg agg<br>Tyr Asp Ala Leu Leu Glu Lys Ile Ile Ser Asp Arg Glu Arg Ser Arg<br>245 250 255 | | 824 |
| agg caa aat cgt gat aag cat ggt ggc ggt aac aat gag gag gcc aag<br>Arg Gln Asn Arg Asp Lys His Gly Gly Gly Asn Asn Glu Glu Ala Lys<br>260 265 270 | | 872 |
| gat ttt ctt gat atg ttg ctt gat gtg atg gag agt ggg gac acg gag<br>Asp Phe Leu Asp Met Leu Leu Asp Val Met Glu Ser Gly Asp Thr Glu<br>275 280 285 | | 920 |
| gtc aaa ttc act aga gag cat ctc aag gct ttg att ctg gat ttc ttc<br>Val Lys Phe Thr Arg Glu His Leu Lys Ala Leu Ile Leu Asp Phe Phe<br>290 295 300 | | 968 |
| acg gcc ggt acg gac aca aca gcc ata gcc acc gag tgg gcc atc gcc<br>Thr Ala Gly Thr Asp Thr Thr Ala Ile Ala Thr Glu Trp Ala Ile Ala<br>305 310 315 320 | | 1016 |
| gag ctc atc aac aac ccg aac gtc ttg aag aag gcc caa gaa gaa ata<br>Glu Leu Ile Asn Asn Pro Asn Val Leu Lys Lys Ala Gln Glu Glu Ile<br>325 330 335 | | 1064 |
| tcc cgg atc atc gga acc aag cgg atc gta caa gaa tcc gac gcc cca<br>Ser Arg Ile Ile Gly Thr Lys Arg Ile Val Gln Glu Ser Asp Ala Pro<br>340 345 350 | | 1112 |
| gac cta ccc tac ctc cag gcc atc atc aag gag acg ttc cgg ctc cac<br>Asp Leu Pro Tyr Leu Gln Ala Ile Ile Lys Glu Thr Phe Arg Leu His<br>355 360 365 | | 1160 |
| cca ccg atc ccg atg ctc tcg cgt aag tcc acc tcc gat tgc acg gtc<br>Pro Pro Ile Pro Met Leu Ser Arg Lys Ser Thr Ser Asp Cys Thr Val<br>370 375 380 | | 1208 |
| aac ggc tac aaa atc caa gcc aag agc ctc ttg ttc gtg aac ata tgg<br>Asn Gly Tyr Lys Ile Gln Ala Lys Ser Leu Leu Phe Val Asn Ile Trp<br>385 390 395 400 | | 1256 |
| tcc atc ggt cga aac cct aat tac tgg gaa agc cct atg gag ttc agg<br>Ser Ile Gly Arg Asn Pro Asn Tyr Trp Glu Ser Pro Met Glu Phe Arg<br>405 410 415 | | 1304 |
| ccc gag cgg ttc ttg gag aag gga cgc gag tcc atc gac gtc aag ggc<br>Pro Glu Arg Phe Leu Glu Lys Gly Arg Glu Ser Ile Asp Val Lys Gly<br>420 425 430 | | 1352 |
| cag cac ttt gag ctc ttg cct ttt ggg acg ggc cgc agg ggc tgt ccc<br>Gln His Phe Glu Leu Leu Pro Phe Gly Thr Gly Arg Arg Gly Cys Pro<br>435 440 445 | | 1400 |
| ggt atg ttg ctg gct ata caa gag gtg gtc agc atc att ggg acc atg<br>Gly Met Leu Leu Ala Ile Gln Glu Val Val Ser Ile Ile Gly Thr Met<br>450 455 460 | | 1448 |
| gtt cag tgc ttc gac tgg aaa ttg gca gat ggt tcg ggc aat aat gtg<br>Val Gln Cys Phe Asp Trp Lys Leu Ala Asp Gly Ser Gly Asn Asn Val<br>465 470 475 480 | | 1496 |
| gac atg acc gaa cgg tct gga ttg acc gct ccg aga gcg ttc gat ctg<br>Asp Met Thr Glu Arg Ser Gly Leu Thr Ala Pro Arg Ala Phe Asp Leu<br>485 490 495 | | 1544 |
| gtt tgc cgg ttg tat cca cgg gtt gac ccg gcc aca ata tcg ggt gct<br>Val Cys Arg Leu Tyr Pro Arg Val Asp Pro Ala Thr Ile Ser Gly Ala<br>500 505 510 512 | | 1592 |
| tgatgtagta gggtgaggcg cgtgttggtg ttttatcttt cggttttgtt ctgttagtat | | 1652 |
| tattatggtc tgtgttgaag cctcaaggat tttaaaaaaa aaaaaaaaaa aaaaaaaaaa | | 1712 |
| aaaaaaaaaa aaaaaaaa | | 1730 |

<210> SEQ ID NO 4
<211> LENGTH: 512
<212> TYPE: PRT
<213> ORGANISM: Torenia hybrida
<220> FEATURE:
<223> OTHER INFORMATION: Amino acid sequence of a protein having an activity to directly convert flavanone to flavone

<400> SEQUENCE: 4

```
Met Asp Thr Val Leu Ile Thr Leu Tyr Thr Ala Leu Phe Val Ile Thr
 1               5                  10                  15

Thr Thr Phe Leu Leu Leu Arg Arg Arg Gly Pro Pro Ser Pro Pro
             20                  25                  30

Gly Pro Leu Ser Leu Pro Ile Ile Gly His Leu His Leu Leu Gly Pro
             35                  40                  45

Arg Leu His His Thr Phe His Glu Phe Ser Leu Lys Tyr Gly Pro Leu
         50                  55                  60

Ile Gln Leu Lys Leu Gly Ser Ile Pro Cys Val Val Ala Ser Thr Pro
 65                  70                  75                  80

Glu Leu Ala Arg Glu Phe Leu Lys Thr Asn Glu Leu Ala Phe Ser Ser
                 85                  90                  95

Arg Lys His Ser Thr Ala Ile Asp Ile Val Thr Tyr Asp Ser Ser Phe
                100                 105                 110

Ala Phe Ser Pro Tyr Gly Pro Tyr Trp Lys Tyr Ile Lys Lys Leu Cys
            115                 120                 125

Thr Tyr Glu Leu Leu Gly Ala Arg Asn Leu Gly His Phe Gln Pro Ile
        130                 135                 140

Arg Asn Leu Glu Val Arg Ser Phe Leu Gln Leu Leu Met His Lys Ser
145                 150                 155                 160

Phe Lys Gly Glu Ser Val Asn Val Thr Asp Glu Leu Val Arg Leu Thr
                165                 170                 175

Ser Asn Val Ile Ser His Met Met Leu Ser Ile Arg Cys Ser Glu Asp
            180                 185                 190

Glu Gly Asp Ala Glu Ala Ala Arg Thr Val Ile Arg Glu Val Thr Gln
        195                 200                 205

Ile Phe Gly Glu Phe Asp Val Thr Asp Ile Ile Trp Phe Cys Lys Lys
210                 215                 220

Phe Asp Leu Gln Gly Ile Lys Lys Arg Ser Glu Asp Ile Gln Arg Arg
225                 230                 235                 240

Tyr Asp Ala Leu Leu Glu Lys Ile Ile Ser Asp Arg Glu Arg Ser Arg
                245                 250                 255

Arg Gln Asn Arg Asp Lys His Gly Gly Asn Asn Glu Glu Ala Lys
            260                 265                 270

Asp Phe Leu Asp Met Leu Leu Asp Val Met Glu Ser Gly Asp Thr Glu
        275                 280                 285

Val Lys Phe Thr Arg Glu His Leu Lys Ala Leu Ile Leu Asp Phe Phe
290                 295                 300

Thr Ala Gly Thr Asp Thr Thr Ala Ile Ala Thr Glu Trp Ala Ile Ala
305                 310                 315                 320

Glu Leu Ile Asn Asn Pro Asn Val Leu Lys Lys Ala Gln Glu Glu Ile
                325                 330                 335

Ser Arg Ile Ile Gly Thr Lys Arg Ile Val Gln Glu Ser Asp Ala Pro
            340                 345                 350

Asp Leu Pro Tyr Leu Gln Ala Ile Ile Lys Glu Thr Phe Arg Leu His
        355                 360                 365

Pro Pro Ile Pro Met Leu Ser Arg Lys Ser Thr Ser Asp Cys Thr Val
370                 375                 380

Asn Gly Tyr Lys Ile Gln Ala Lys Ser Leu Leu Phe Val Asn Ile Trp
```

-continued

```
                385                 390                 395                 400
Ser Ile Gly Arg Asn Pro Asn Tyr Trp Glu Ser Pro Met Glu Phe Arg
                    405                 410                 415

Pro Glu Arg Phe Leu Glu Lys Gly Arg Glu Ser Ile Asp Val Lys Gly
                420                 425                 430

Gln His Phe Glu Leu Leu Pro Phe Gly Thr Gly Arg Arg Gly Cys Pro
            435                 440                 445

Gly Met Leu Leu Ala Ile Gln Glu Val Val Ser Ile Ile Gly Thr Met
        450                 455                 460

Val Gln Cys Phe Asp Trp Lys Leu Ala Asp Gly Ser Gly Asn Asn Val
465                 470                 475                 480

Asp Met Thr Glu Arg Ser Gly Leu Thr Ala Pro Arg Ala Phe Asp Leu
                485                 490                 495

Val Cys Arg Leu Tyr Pro Arg Val Asp Pro Ala Thr Ile Ser Gly Ala
                500                 505                 510
```

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
aaataggatc caagcatgga cacagtctta a          31

<210> SEQ ID NO 6
<211> LENGTH: 35
<212> TYPE: DNA
<213> ORGANISM: Artificial Sequence
<220> FEATURE:
<223> OTHER INFORMATION: Primer

<400> SEQUENCE: 6
cccttctaga tcaagcaccc gatattgtgg ccggg          35

<210> SEQ ID NO 7
<211> LENGTH: 1770
<212> TYPE: DNA
<213> ORGANISM: Perilla frutescens
<220> FEATURE:
<223> OTHER INFORMATION: Nucleotide sequence encoding a protein having
      an activity to directly convert flavanone to flavone

<400> SEQUENCE: 7

```
tgtcgacgga gcaagtggaa atg gca ctg tac gcc gcc ctc ttc ctc ctg tcc     53
                     Met Ala Leu Tyr Ala Ala Leu Phe Leu Leu Ser
                      1               5                  10 gcc gcc gtg gtc cgc tcc gtt ctg gat cga aaa cgc ggg cgg ccg ccc       101
Ala Ala Val Val Arg Ser Val Leu Asp Arg Lys Arg Gly Arg Pro Pro
                15                  20                  25 tac cct ccc ggg ccg ttc cct ctt ccc atc atc ggc cac tta cac ctc       149
Tyr Pro Pro Gly Pro Phe Pro Leu Pro Ile Ile Gly His Leu His Leu
            30                  35                  40 ctc ggg ccg aga ctc cac caa acc ttc cac gat ctg tcc caa cgg tac       197
Leu Gly Pro Arg Leu His Gln Thr Phe His Asp Leu Ser Gln Arg Tyr
        45                  50                  55 ggg ccc tta atg cag ctc cgc ctc ggg tcc atc cgc tgc gtc att gct       245
Gly Pro Leu Met Gln Leu Arg Leu Gly Ser Ile Arg Cys Val Ile Ala
    60                  65                  70                  75 gcc tcg ccg gag ctc gcc aag gaa tgc ctc aag aca cac gag ctc gtc       293
```

```
Ala Ser Pro Glu Leu Ala Lys Glu Cys Leu Lys Thr His Glu Leu Val
             80              85                  90 ttc tcc tcc cgc aaa cac tcc acc gcc att gat atc gtc acc tac gat      341
Phe Ser Ser Arg Lys His Ser Thr Ala Ile Asp Ile Val Thr Tyr Asp
             95                 100                 105 tca tcc ttc gct ttc tct ccc tac ggg cct tac tgg aaa ttc atc aag      389
Ser Ser Phe Ala Phe Ser Pro Tyr Gly Pro Tyr Trp Lys Phe Ile Lys
        110                 115                 120 aaa tta tgc acc tac gag ctg ctc ggg gcc cga aat ctc gcc cac ttt      437
Lys Leu Cys Thr Tyr Glu Leu Leu Gly Ala Arg Asn Leu Ala His Phe
        125                 130                 135 cag ccc atc agg act ctc gaa gtc aag tct ttc ctc caa att ctt atg      485
Gln Pro Ile Arg Thr Leu Glu Val Lys Ser Phe Leu Gln Ile Leu Met
140                 145                 150                 155 cgc aag ggt gaa tcg ggg gag agc ttc aac gtg act gag gag ctc gtg      533
Arg Lys Gly Glu Ser Gly Glu Ser Phe Asn Val Thr Glu Glu Leu Val
                160                 165                 170 aag ctg acg agc aac gtc ata tcg cat atg atg ctg agc ata cgg tgt      581
Lys Leu Thr Ser Asn Val Ile Ser His Met Met Leu Ser Ile Arg Cys
                175                 180                 185 tca gag acg gag tcg gag gcg gag gcg gcg agg acg gtg att cgg gag      629
Ser Glu Thr Glu Ser Glu Ala Glu Ala Ala Arg Thr Val Ile Arg Glu
            190                 195                 200 gtc acg cag ata ttt ggg gag ttc gac gtc tcc gac atc ata tgg ctt      677
Val Thr Gln Ile Phe Gly Glu Phe Asp Val Ser Asp Ile Ile Trp Leu
            205                 210                 215 tgt aag aac ttc gat ttc caa ggt ata agg aag cgg tcc gag gat atc      725
Cys Lys Asn Phe Asp Phe Gln Gly Ile Arg Lys Arg Ser Glu Asp Ile
220                 225                 230                 235 cag agg aga tat gat gct ctg ctg gag aag atc atc acc gac aga gag      773
Gln Arg Arg Tyr Asp Ala Leu Leu Glu Lys Ile Ile Thr Asp Arg Glu
                240                 245                 250 aag cag agg cgg acc cac ggc ggc ggt ggc ggc ggc ggg gaa gcc aag      821
Lys Gln Arg Arg Thr His Gly Gly Gly Gly Gly Gly Gly Glu Ala Lys
                255                 260                 265 gat ttt ctt gac atg ttc ctc gac ata atg gag agc ggg aaa gcc gaa      869
Asp Phe Leu Asp Met Phe Leu Asp Ile Met Glu Ser Gly Lys Ala Glu
            270                 275                 280 gtt aaa ttc acg agg gag cat ctc aaa gct ttg att ctg gat ttc ttc      917
Val Lys Phe Thr Arg Glu His Leu Lys Ala Leu Ile Leu Asp Phe Phe
285                 290                 295 acc gcc ggc acc gac acg acg gcg atc gtg tgt gaa tgg gcg ata gca      965
Thr Ala Gly Thr Asp Thr Thr Ala Ile Val Cys Glu Trp Ala Ile Ala
300                 305                 310                 315 gaa gtg atc aac aat cca aat gtg ttg aag aaa gct caa gaa gag att     1013
Glu Val Ile Asn Asn Pro Asn Val Leu Lys Lys Ala Gln Glu Glu Ile
                320                 325                 330 gcc aac atc gtc gga ttc gac aga att ctg caa gaa tcc gac gcc cca     1061
Ala Asn Ile Val Gly Phe Asp Arg Ile Leu Gln Glu Ser Asp Ala Pro
                335                 340                 345 aat ctg ccc tac ctt caa gcc ctc atc aaa gaa aca ttc cgg ctc cac     1109
Asn Leu Pro Tyr Leu Gln Ala Leu Ile Lys Glu Thr Phe Arg Leu His
            350                 355                 360 cct cca atc cca atg ctg gcg agg aaa tcg atc tcc gac tgc gtc atc     1157
Pro Pro Ile Pro Met Leu Ala Arg Lys Ser Ile Ser Asp Cys Val Ile
365                 370                 375 gac ggc tac atg att ccg gcc aac acg ctg ctc ttc gtc aac ctc tgg     1205
Asp Gly Tyr Met Ile Pro Ala Asn Thr Leu Leu Phe Val Asn Leu Trp
380                 385                 390                 395
```

```
tcc atg ggg cgg aac cct aaa atc tgg gac tac ccg acg gcg ttc cag      1253
Ser Met Gly Arg Asn Pro Lys Ile Trp Asp Tyr Pro Thr Ala Phe Gln
            400                 405                 410 ccg gag agg ttt ctg gag aag gaa aag gcc gcc atc gat gtt aaa ggg      1301
Pro Glu Arg Phe Leu Glu Lys Glu Lys Ala Ala Ile Asp Val Lys Gly
                415                 420                 425 cag cat ttt gag ctg cta ccg ttc gga acg ggc agg aga ggc tgc cca      1349
Gln His Phe Glu Leu Leu Pro Phe Gly Thr Gly Arg Arg Gly Cys Pro
            430                 435                 440 ggg atg ctt tta gcc att cag gag gtg gtc atc ata att ggg acg atg      1397
Gly Met Leu Leu Ala Ile Gln Glu Val Val Ile Ile Ile Gly Thr Met
        445                 450                 455 att caa tgc ttc gat tgg aag ctg ccc gac ggc tcc ggc cat gtt gat      1445
Ile Gln Cys Phe Asp Trp Lys Leu Pro Asp Gly Ser Gly His Val Asp
460                 465                 470                 475 atg gca gaa cgg cca ggg ctc acg gca ccg cga gag acc gat ttg ttt      1493
Met Ala Glu Arg Pro Gly Leu Thr Ala Pro Arg Glu Thr Asp Leu Phe
                480                 485                 490 tgc cgt gtg gtg ccg cga gtt gat ccg ttg gtt gtt tcc acc cag          1538
Cys Arg Val Val Pro Arg Val Asp Pro Leu Val Val Ser Thr Gln
            495                 500                 505 tgatcacccc ctttaaattt attaatgata tattttatt ttgagaaaaa ataaaaatgc     1598
taattgtttt gtttcatgat gtaattgtta attagtttct attgtgcgct gtcgcgtgtc    1658
gcgtggctta agataagatt gtatcattgg tacctaggat gtattttcat tttcaataaa    1718
ttattttgtg ctgtgtatat taaaaaaaaa aaagaaaaaa aaaaaaaaaa aa            1770

<210> SEQ ID NO 8
<211> LENGTH: 506
<212> TYPE: PRT
<213> ORGANISM: Perilla frutescens
<220> FEATURE:
<223> OTHER INFORMATION: Amino acid sequence of a protein having
      an activity to directly convert flavanone to flavone

<400> SEQUENCE: 8

Met Ala Leu Tyr Ala Ala Leu Phe Leu Leu Ser Ala Val Val Arg
 1               5                  10                  15

Ser Val Leu Asp Arg Lys Arg Gly Arg Pro Tyr Pro Pro Gly Pro
                20                  25                  30

Phe Pro Leu Pro Ile Ile Gly His Leu His Leu Leu Gly Pro Arg Leu
            35                  40                  45

His Gln Thr Phe His Asp Leu Ser Gln Arg Tyr Gly Pro Leu Met Gln
        50                  55                  60

Leu Arg Leu Gly Ser Ile Arg Cys Val Ile Ala Ala Ser Pro Glu Leu
65                  70                  75                  80

Ala Lys Glu Cys Leu Lys Thr His Glu Leu Val Phe Ser Ser Arg Lys
                85                  90                  95

His Ser Thr Ala Ile Asp Ile Val Thr Tyr Asp Ser Ser Phe Ala Phe
            100                 105                 110

Ser Pro Tyr Gly Pro Tyr Trp Lys Phe Ile Lys Lys Leu Cys Thr Tyr
        115                 120                 125

Glu Leu Leu Gly Ala Arg Asn Leu Ala His Phe Gln Pro Ile Arg Thr
    130                 135                 140

Leu Glu Val Lys Ser Phe Leu Gln Ile Leu Met Arg Lys Gly Glu Ser
145                 150                 155                 160

Gly Glu Ser Phe Asn Val Thr Glu Glu Leu Val Lys Leu Thr Ser Asn
                165                 170                 175
```

```
Val Ile Ser His Met Met Leu Ser Ile Arg Cys Ser Glu Thr Glu Ser
            180                 185                 190

Glu Ala Glu Ala Ala Arg Thr Val Ile Arg Glu Val Thr Gln Ile Phe
            195                 200                 205

Gly Glu Phe Asp Val Ser Asp Ile Ile Trp Leu Cys Lys Asn Phe Asp
            210                 215                 220

Phe Gln Gly Ile Arg Lys Arg Ser Glu Asp Ile Gln Arg Arg Tyr Asp
225                 230                 235                 240

Ala Leu Leu Glu Lys Ile Ile Thr Asp Arg Glu Lys Gln Arg Arg Thr
            245                 250                 255

His Gly Gly Gly Gly Gly Gly Glu Ala Lys Asp Phe Leu Asp Met
            260                 265                 270

Phe Leu Asp Ile Met Glu Ser Gly Lys Ala Glu Val Lys Phe Thr Arg
            275                 280                 285

Glu His Leu Lys Ala Leu Ile Leu Asp Phe Phe Thr Ala Gly Thr Asp
            290                 295                 300

Thr Thr Ala Ile Val Cys Glu Trp Ala Ile Ala Glu Val Ile Asn Asn
305                 310                 315                 320

Pro Asn Val Leu Lys Lys Ala Gln Glu Glu Ile Ala Asn Ile Val Gly
            325                 330                 335

Phe Asp Arg Ile Leu Gln Glu Ser Asp Ala Pro Asn Leu Pro Tyr Leu
            340                 345                 350

Gln Ala Leu Ile Lys Glu Thr Phe Arg Leu His Pro Pro Ile Pro Met
            355                 360                 365

Leu Ala Arg Lys Ser Ile Ser Asp Cys Val Ile Asp Gly Tyr Met Ile
            370                 375                 380

Pro Ala Asn Thr Leu Leu Phe Val Asn Leu Trp Ser Met Gly Arg Asn
385                 390                 395                 400

Pro Lys Ile Trp Asp Tyr Pro Thr Ala Phe Gln Pro Glu Arg Phe Leu
            405                 410                 415

Glu Lys Glu Lys Ala Ala Ile Asp Val Lys Gly Gln His Phe Glu Leu
            420                 425                 430

Leu Pro Phe Gly Thr Gly Arg Arg Gly Cys Pro Gly Met Leu Leu Ala
            435                 440                 445

Ile Gln Glu Val Val Ile Ile Ile Gly Thr Met Ile Gln Cys Phe Asp
            450                 455                 460

Trp Lys Leu Pro Asp Gly Ser Gly His Val Asp Met Ala Glu Arg Pro
465                 470                 475                 480

Gly Leu Thr Ala Pro Arg Glu Thr Asp Leu Phe Cys Arg Val Val Pro
            485                 490                 495

Arg Val Asp Pro Leu Val Val Ser Thr Gln
            500                 505
```

DNAS CODING FOR FLAVONE SYNTHASE, METHODS OF USING FLAVONE SYNTHASE DNAS, AND PLANTS, FLOWERS, AND VECTORS CONTAINING FLAVONE SYNTHASE DNAS

CROSS REFERENCE TO RELATED APPLICATIONS

This application is a divisional of U.S. patent application Ser. No. 09/672,785, filed Sep. 29, 2000, now U.S. Pat. No. 6,596,927, which is a continuation of International Application Nos. PCT/JP00/00490 and PCT/JP00/04379 filed in WIPO on Jan. 28, 1999 and Jun. 30, 2000, respectively, and claims benefit of Japanese patent applications 11-22427 and 11-205229 filed respectively on Jan. 29, 1999 and Jul. 19, 1999; the entire contents of which are hereby incorporated by reference.

TECHNICAL FIELD

The present invention relates to the control and utilization of biosynthesis of flavones, which have effects on flower color, protection from ultraviolet ray, symbiosis with microorganisms, etc. in plants, by a genetic engineering technique. More specifically, it relates to genes encoding proteins with activity of synthesizing flavones from flavanones, and to their utilization.

BACKGROUND ART

The abundance of different flower colors is one of the pleasant aspects of life that enriches human minds and hearts. It is expected to increase food production to meet future population increase by the means of accelerating the growth of plants through symbiosis with microorganisms, or by increasing the number of nitrogen-fixing leguminous bacteria, thus improving the plant productivity as a result of increasing the content of nitrogen in the soil. Elimination or reduction of the use of agricultural chemicals is also desirable to achieve more environmentally friendly agriculture, and this requires improvement of the soil by the above-mentioned biological means, as well as higher resistance of plants against microbial infection. Another desired goal is to obtain plants with high protective functions against ultraviolet rays as a means of protecting the plants from the destruction of the ozone layer.

"Flavonoid" is a general term for a group of compounds with a C6-C3-C6 carbon skeleton, and they are widely distributed throughout plant cells. Flavonoids are known to have such functions as attracting insects and other pollinators, protecting plant from ultraviolet rays, and participating in interaction with soil microorganisms (BioEssays, 16 (1994), Koes at al., p. 123; Trends in Plant Science, 1 (1997), Shirley, B. W., p. 377).

Of flavonoids, flavone plays an important role in interaction of plants with microorganisms, especially in legumes, where they participate in the initial steps of the symbiosis with leguminous bacteria (Plant Cell, 7 (1995), Dixon and Paiva, p. 1085; Annu. Rev. Phytopathol., 33 (1995), Spaink, p. 345). Flavones in petals play a role in recognition by insects and act as copigments which form complexes with anthocyanins. (Gendai Kagaku, (May, 1998), Honda and Saito, p. 25; Prog. Chem. Org. Natl. Prod., 52 (1987), Goto, T., p. 114). It is known that when flavone forms a complex with anthocyanin, the absorption maximum of the anthocyanin shifts toward the longer wavelength, i.e. toward blue.

The biosynthesis pathways for flavonoids have been widely studied (Plant Cell, 7 (1995), Holton and Cornish, p. 1071), and the genes for all of the enzymes involved in the biosynthesis of anthocyanidin 3-glucoside and flavonol, for example, have been isolated. However, the genes involved in the biosynthesis of flavones have not yet been isolated. The enzymes that synthesize flavones include those belonging to the dioxygenase family that depends on 2-oxoglutaric acid (flavone synthase I) and monooxygenase enzymes belonging to the cytochrome P450 family (flavone synthase II). These groups of enzymes are completely different enzymes with no structural homology.

It has been reported that in parsley, 2-oxoglutaric acid-dependent dioxygenase catalyzes a reaction which produces apigenin, a flavone, from naringenin, a flavanone (Z. Naturforsch., 36c (1981), Britsch et al., p. 742; Arch. Biochem. Biophys., 282 (1990), Britsch, p. 152). The other type, flavone synthase II, is known to exist in snapdragon (Z. Naturforsch., 36c (1981), Stotz and Forkmann, p. 737) and soybean (Z. Naturforsch., 42c (1987), Kochs and Grisebach, p. 343; Planta, 171 (1987), Kochs et al., p. 519). A correlation has been recently reported between a gene locus and flavone synthase II activity in the petals of gerbera (Phytochemistry, 49 (1998), Martens and Forkmann, p. 1953). However, there are no reports that the genes for these flavone synthases I and II were isolated or that flavone synthase II was highly purified.

The properties of a cytochrome P450 protein, which had licodione-synthesizing activity that was induced when cultured cells of licorice (*Glycyrrhiza echinata*) were treated with an elicitor, were investigated. The protein is believed to catalyze the hydroxylation of 2-position of liquiritigenin which is a 5-deoxyflavanone, followed by non-enzymatic hemiacetal ring opening to produce licodione (Plant Physiol., 105 (1994), Otani et al., p. 1427). For cloning of licodione synthase, a cDNA library was prepared from elicitor-treated *Glycyrrhiza* cultured cells, and 8 gene fragments encoding cytochrome P450 were cloned (Plant Science, 126 (1997), Akashi et al., p. 39).

From these fragments there were obtained two different full-length cDNA sequences, each encoding a cytochrome P450, which had been unknown until that time. Specifically, they were CYPGe-3 (cytochrome P450 No.CYP81E1) and CYPGe-5 (cytochrome P450 No.CYP93B1, hereinafter indicated as CYP93B1) (Plant Physiol., 115 (1997), Akashi et al., p. 1288). By further expressing the CYP93B1 cDNA in a system using cultured insect cells, the protein derived from the gene was shown to catalyze the reaction synthesizing licodione from liquiritigenin, a flavanone, and 2-hydroxynaringenin from naringenin, also a flavanone.

2-Hydroxynaringenin was converted to apigenin, a flavone, by acid treatment with 10% hydrochloric acid (room temperature, 2 hours). Also, eriodictyol was converted to luteolin, a flavone, by reacting eriodictyol with microsomes of CYP93B1-expressing yeast followed by acid treatment. It was therefore demonstrated that the cytochrome P450 gene encodes the function of flavanone 2-hydroxylase activity (FEBS Lett., 431 (1998), Akashi et al., p. 287). Here, production of apigenin from naringenin required CYP93B1 as well as another unknown enzyme, so that it was concluded that a total of two enzymes were necessary.

However, no genes have yet been identified for enzymes with activity of synthesizing flavones (such as apigenin) directly from flavanones (such as naringenin) without acid treatment. Thus, despite the fact that flavones have numerous functions in plants, no techniques have yet been reported for controlling their biosynthesis in plants, and improving the biofunctions in which flavones are involved, such as flower color. The discovery of an enzyme which by itself can accomplish synthesis of flavones from flavanones and acquisition of its gene, and introduction of such a gene into plants, would be more practical and industrially applicable than the introduction into a plant of genes for two enzymes involved in the synthesis of flavones from flavanones.

DISCLOSURE OF THE INVENTION

It is an aim of the present invention to provide flavone synthase genes, preferably flavone synthase II genes, and more preferably genes for flavone synthases with activity of synthesizing flavones directly from flavanones. The obtained flavone synthase genes may be introduced into plants and over-expressed to alter flower colors.

Moreover, in the petals of flowers that naturally contain large amounts of flavones, it is expected that controlling expression of the flavone synthase genes by an antisense method or a cosuppression method can also alter flower colors. Also, expression of the flavone synthase genes in the appropriate organs, in light of the antibacterial activity of flavones and their interaction with soil microorganisms, will result in an increase in the antibacterial properties of plants and improvement in the nitrogen fixing ability of legumes due to promoted symbiosis with rhizosphere microorganisms, as well as a protective effect against ultraviolet rays and light.

The present invention therefore provides genes encoding proteins that can synthesize flavones directly from flavanones. The genes are, specifically, genes encoding flavone synthase II that can synthesize flavones from flavanones by a single-enzyme reaction (hereinafter referred to as "flavone synthase II").

More specifically, the present invention provides genes encoding P450 proteins having the amino acid sequences listed as SEQ.ID. No. 2, 4 or 8 of the Sequence Listing and possessing activity of synthesizing flavones from flavanones, or genes encoding proteins having amino acid sequences modified by additions or deletions of one or more amino acids and/or a substitution with different amino acids in said amino acid sequence, and possessing activity of synthesizing flavones from flavanones.

The invention further provides a gene encoding proteins having amino acid sequences with at least 55% identity with the amino acid sequences listed as SEQ.ID. No. 2, 4 or 8 of the Sequence Listing and possessing activity of synthesizing flavones from flavanones.

The invention still further provides genes encoding proteins possessing activity of synthesizing flavones from flavanones, and hybridizing with all or a part of the nucleotide sequences listed as SEQ.ID. No. 1, 3 or 7 of the Sequence List under the conditions of 5×SSC, 50° C.

The invention still further provides a vector, particularly an expression vector, containing any one of the aforementioned genes.

The invention still further provides a host transformed with the aforementioned vector.

The invention still further provides a protein encoded by any of the aforementioned genes.

The invention still further provides a process for producing the aforementioned protein which is characterized by culturing or growing the aforementioned host, and collecting the protein with flavone-synthesizing activity from the host.

The invention still further provides a plant into which any one of the aforementioned genes has been introduced, or progenies of the plant or a tissue thereof, such as cut flowers, which exhibit the same properties.

The invention still further provides a method of altering amounts and compositions of flavonoid using the aforementioned genes; a method of altering amounts of flavones using the aforementioned genes; a method of altering flower colors using the aforementioned genes; a method of bluing the color of flowers using the aforementioned genes; a method of reddening the color of flowers using the aforementioned genes; a method of modifying the photosensitivity of plants using the aforementioned genes; and a method of controlling the interaction between plants and microbes using the aforementioned genes.

Figure 1:
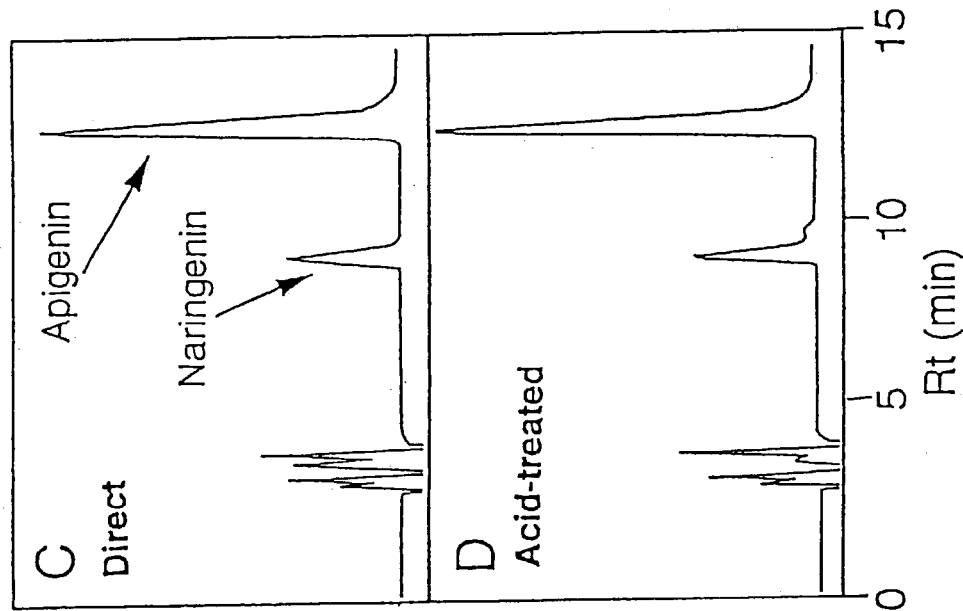
FIG. 1 is a chromatogram showing the results of HPLC analysis of products obtained from a substrate, naringenin, using proteins encoded by CYP93B1 and TFNS5.
Figure 1:
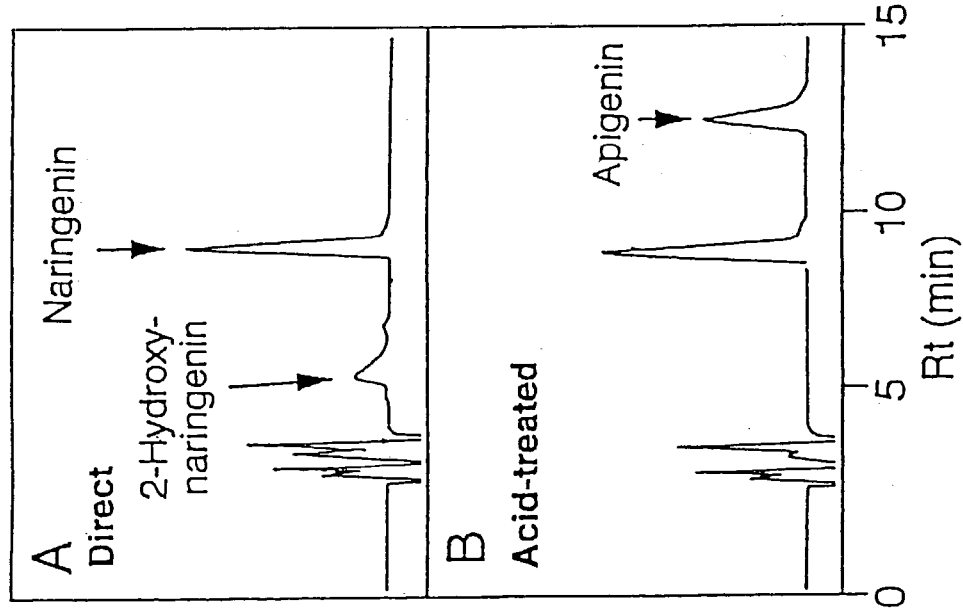

A and B: Obtained by adding a crude enzyme fraction of CYP93B1-expressing yeast.

C and D: Obtained by adding a crude enzyme fraction of TFNS5-expressing yeast.

A and C: Direct products obtained by addition of enzyme fraction.

B: Products obtained by acid treatment after reaction of A.

D: Products obtained by acid treatment after reaction of C.

EMBODIMENTS FOR CARRYING OUT THE INVENTION

Flavanone 2-hydroxylase encoded by the *Glycyrrhiza* CYP93B1 gene produces 2-hydroxyflavanones from flavanones as the substrates, and the products are converted to flavones by acid treatment. The present inventors viewed that it would be possible to obtain a gene encoding a flavone synthase II, which was an object of the invention, by using the *Glycyrrhiza*-derived cDNA, CYP93B1 for screening of a cDNA library of, for example, a flower containing a large amount of flavones, to thus obtain cDNA encoding proteins with activity of synthesizing flavones directly from flavanones as substrates.

According to the invention, a cDNA library of snapdragon which contains a large amount of flavones is screened using the *Glycyrrhiza*-derived cDNA, CYP93B1 as a probe, to obtain cDNA encoding a novel cytochrome P450 (see Example 1). The snapdragon cDNA, ANFNS2, obtained in this manner and the *Glycyrrhiza* CYP93B1 cDNA were then used as a mixed probe to obtain TFNS5, a cDNA encoding a novel cytochrome P450, from a cDNA library of torenia flower petals (see Example 2).

The torenia-derived cDNA was expressed in yeast and reacted with naringenin, a flavanone, as a substrate which resulted in production not of 2-hydroxynaringenin but rather of the flavone apigenin, without acid treatment (see Example 3). In other words, this enzyme directly produced flavones from flavanones without acid treatment, and its gene was confirmed to be a flavone synthase II which had never been cloned. The amino acid sequence encoded by the snapdragon-derived ANFNS2 of Example 1 exhibited high identity of 77% with the flavone synthase II encoded by TFNS5, and it exhibited the enzyme activity of flavone synthase II (Example 4). In addition, since an amino acid sequence encoded by perilla-derived cDNA also exhibited high identity of 76% and 75% with TFNS5 and ANFNS2, respectively (Example 8), it is speculated that the protein encoded by this cDNA also possesses the same enzymatic activity as the flavone synthases encoded by TFNS5 and ANFNS2.

The genes of the present invention may be, for example, one encoding the amino acid sequences listed as SEQ.ID. No. 2, 4 or 8 of the Sequence Listing. However, it is known that proteins whose amino acid sequences are modified by additions or deletions of multiple amino acids and/or substitutions with different amino acids can maintain the same enzyme activity as the original protein. Consequently, proteins having the amino acid sequences listed as SEQ.ID. No. 2, 4 or 8 of the Sequence Listing wherein the amino acid sequence is modified by additions or deletions of one or more amino acids and/or substitutions with different amino acids, and genes encoding those proteins, are also encompassed by the present invention so long as they maintain the activity of producing flavones directly from flavanones.

The present invention also relates to genes that have the nucleotide sequences listed as SEQ.ID. Nos. 1, 3 and 7 and nucleotide sequences encoding the amino acid sequences listed therein, or that hybridize with portions of their nucleotide sequences under conditions of 5×SSC, 50° C., for example, providing they encode proteins possessing activity of producing flavones from flavanones. The suitable hybridization temperature will differ depending on nucleotide sequences and the length of nucleotide sequences, and for example, when the probe used is a DNA fragment comprising 18 bases coding for 6 amino acids, the temperature is preferably not higher than 50° C.

A gene selected by such hybridization may be a naturally derived one, such as a plant-derived gene, for example, a gene derived from snapdragon, torenia or perilla; it may also be a gene from another plant, such as gentian, verbena, chrysanthemum, iris, or the like. A gene selected by hybridization may be cDNA or genomic DNA.

The invention also relates to genes encoding proteins that have amino acid sequences with identity of at least 55%, preferably at least 70%, such as 80% or greater and even 90% or greater, with any one of the amino acid sequences listed as SEQ.ID. Nos. 2, 4 or 8 of the Sequence Listing, and that possess activity of synthesizing flavones from flavanones.

A gene with the natural nucleotide sequence can be obtained by screening of a cDNA library, for example, as demonstrated in detail in the examples. DNA encoding enzymes with modified amino acid sequences can be synthesized using common site-directed mutagenesis or a PCR method, using DNA with a natural nucleotide sequence as a starting material. For example, a DNA fragment into which a modification is to be introduced may be obtained by restriction enzyme treatments of natural cDNA or genomic DNA and then used as a template for site-directed mutagenesis or PCR using a primer having the desired mutation introduced therein, to obtain a DNA fragment having the desired modification introduced therein. Mutation-introduced DNA fragments may then be linked to a DNA fragment encoding another portion of a target enzyme.

Alternatively, in order to obtain DNA encoding an enzyme consisting of a shortened amino acid sequence, for example, DNA encoding an amino acid sequence which is longer than the aimed amino acid sequence, such as the full length amino acid sequence, may be cut with desired restriction endonucleases, and if the DNA fragment obtained thereby does not encode the entire target amino acid sequence, it may be linked with synthesized DNA comprising the rest of the sequence.

Thus obtained genes may be expressed in an expression system using *E. coli* or yeast and its enzyme activity measured to confirm that the obtained gene encodes flavone synthase. By expressing the gene, it is also possible to obtain the flavone synthase protein as the gene product. Alternatively, it is also possible to obtain a flavone synthase protein even using antibodies for a full or a partial amino acid sequence listed as SEQ.ID. No. 2, 4 or 8, and such antibodies may be used for cloning of a flavone synthase gene in another organism.

Consequently, the invention also relates to recombinant vectors, and especially expression vectors, containing the aforementioned genes, and to hosts transformed by these vectors. The hosts used may be prokaryotic or eukaryotic organisms. Examples of prokaryotic organisms that may commonly be used as hosts include bacteria belonging to the genus *Escherichia*, such as *Escherichia coli*, and microorganisms belonging to the genus *Bacillus*, such as *Bacillus subtilis*.

Examples of eukaryotic hosts that may be used include lower eukaryotic organisms, for example, eukaryotic microorganisms, for example, *Eumycota* such as yeast and filamentous fungi. As yeast there may be mentioned microorganisms belonging to the genus *Saccharomyces*, such as *Saccharomyces cerevisiae*, and as filamentous fungi there may be mentioned microorganisms belonging to the genus *Aspergillus*, such as *Aspergillus oryzae* and *Aspergillus niger* and microorganisms belonging to the genus *Penicillium*. Animal cells and plant cells may also be used, the animal cells being cell lines from mice, hamsters, monkeys or humans. Insect cells, such as silkworm cells, or the adult silkworms themselves, may also be used.

The expression vectors of the invention will include expression regulating regions such as a promoter and a terminator, a replication origin, etc., depending on the type of hosts into which they are to be introduced. Examples of promoters for bacterial expression vectors which may be used include conventional promoters such as trc promoter, tac promoter, lac promoter, etc., examples of yeast promoters that may be used include glyceraldehyde-3-phosphate dehydrogenase promoter, PH05 promoter, etc., and examples of filamentous fungi promoters that may be used include amylase promoter, trpC, etc. Examples of animal cell host promoters that may be used include viral promoters such as SV40 early promoter, SV40 late promoter, etc.

The expression vector may be prepared according to a conventional method using restriction endonucleases, ligases and the like. The transformation of a host with an expression vector may also be carried out according to conventional methods.

The hosts transformed by the expression vector may be cultured, cultivated or raised, and the target protein may be recovered and purified from the cultured product, etc. according to conventional methods such as filtration, centrifugal separation, cell crushing, gel filtration chromatography, ion-exchange chromatography and the like.

The present specification throughout discusses flavone synthases II derived from snapdragon, torenia and perilla that are capable of synthesizing flavones directly from flavanones, and it is also known that the cytochrome P450 genes constitute a superfamily (DNA and Cell Biology, 12 (1993), Nelson et al., p. 1) and that cytochrome P450 proteins within the same family have 40% or greater identity in their amino acid sequences while cytochrome P450 proteins within a subfamily have 55% or greater identity in their amino acid sequences, and their genes hybridize to each other (Pharmacogenetics, 6 (1996), Nelson et al., p. 1).

For example, a gene for flavonoid 3',5'-hydroxylase, which was a type of cytochrome P450 and participated in the pathway of flavonoid synthesis, was first isolated from petunias (Nature, 366 (1993), Holton et al., p. 276), and the petunia flavonoid 3',5'-hydroxylase gene was used as a probe to easily isolate a flavonoid 3',5'-hydroxylase gene from gentian (Plant Cell Physiol., 37 (1996), Tanaka et al., p. 711), prairie-gentian, bellflower (WO93/18155 (1993), Kikuchi et al.), lavender, torenia and verbena (Shokubutsu no Kagaku Chosetsu, 33 (1998), Tanaka et al., p. 55).

Thus, a part or all of any of the flavone synthase II genes of the invention derived from snapdragon, torenia or perilla, which are capable of synthesizing flavones directly from flavanones, can be used as a probe, in order to obtain flavone synthase II genes capable of synthesizing flavones directly from flavanones, from different species of plants. Furthermore, by purifying the snapdragon-, torenia- or perilla-derived flavone synthase II enzymes described in this specification which can synthesize flavones directly from flavanones, and obtaining antibodies against the enzymes by conventional methods, it is possible to obtain different flavone synthase II proteins that react with the antibodies, and obtain genes coding for those proteins.

Consequently, the present invention is not limited merely to snapdragon-, torenia- or perilla-derived genes for flavone synthases II capable of synthesizing flavones directly from flavanones, but further relates to flavone synthases II derived from numerous other plants, which are capable of synthesizing flavones directly from flavanones. The sources for such flavone synthase II genes may be, in addition to snapdragon, torenia and perilla described here, also gentian, verbena, chrysanthemum, iris, commelina, centaurea, salvia, nemophila and the like, although the scope of the invention is not limited to these plants.

The invention still further relates to plants whose colors are modified by introducing a gene or genes for flavone synthases II that can synthesize flavones directly from flavanones, and to progenies of the plants or their tissues, which may also be in the form of cut flowers. By using the flavone synthases II or their genes which have been cloned according to the invention, it is possible to produce flavones in plant species or varieties that otherwise produce little or absolutely no flavones. By expressing the flavone synthase II gene or the genes in flower petals, it is possible to increase the amount of flavones in the flower petals, thus allowing the colors of the flowers to be modified toward the blue, for example.

Conversely, by repressing synthesis of flavones in flower petals, it is possible to modify the colors of the flowers toward the red, for example. However, flavones have myriad effects on flower colors, and the changes in flower colors are therefore not limited to those mentioned here. With the current level of technology, it is possible to introduce a gene into a plant and express the gene in a constitutive or tissue-specific manner, while it is also possible to repress the expression of a target gene by an antisense method or a cosuppression method.

As examples of transformable plants there may be mentioned rose, chrysanthemum, carnation, snapdragon, cyclamen, orchid, prairie-gentian, freesia, gerbera, gladiolus, baby's breath, kalanchoe, lily, pelargonium, geranium, petunia, torenia, tulip, rice, barley, wheat, rapeseed, potato, tomato, poplar, banana, eucalyptus, sweet potato, soybean, alfalfa, lupin, corn, etc., but there is no limitation to these.

Because flavones have various physiological activities as explained above, they can impart new physiological activity or economic value to plants. For example, by expressing the gene to produce flavones in roots, it is possible to promote growth of microorganisms that are beneficial for the plant, and thus promote growth of the plant. It is also possible to synthesize flavones that exhibit physiological activity in humans, animals or insects.

EXAMPLES

The invention will now be explained in further detail by way of the following examples. Unless otherwise specified, the molecular biological methods were carried out according to Molecular Cloning (Sambrook et al., 1989).

Example 1

Cloning of Snapdragon Flavone Synthase II Gene

RNA was extracted from about 5 g of young buds of a Yellow Butterfly snapdragon (commercial name by Sakata-no-Tane, KK.), and polyA+ RNA was obtained by an Oligotex. This polyA+ RNA was used as a template to prepare a cDNA library using a Lambda ZAPII cDNA Library Synthesis Kit (Stratagene) by the method recommended by Stratagene (Stratagene Instruction Manual, Revision #065001). The cDNA library was screened using the full length cDNA CYP93B1 as the probe. The screening and detection of positive clones were carried out using a DIG-DNA-labeling and detection kit (Boehringer) based on the method recommended by the same company, under a low stringent condition.

Specifically, a hybridization buffer (5×SSC, 30% formamide, 50 mM sodium phosphate buffer (pH 7.0), 1% SDS, 2% blocking reagent (Boehringer), 0.1% lauroylsarcosine, 80 μg/ml salmon sperm DNA) was used for prehybridization at 42° C. for 2 hours, after which the DIG-labeled probe was added and the mixture was kept overnight. The membrane was rinsed in 5×SSC rinsing solution containing 1% SDS at 65° C. for 1.5 hours. One positive clone was obtained, and it was designated as ANFNS1. Upon determining the nucleotide sequence at the 5' end of ANFNS1 it was expected that ANFNS1 encodes a sequence with high identity with the flavanone 2-hydroxylase encoded by licorice CYP93B1, and it was assumed that it encoded a P450 with a function similar to that of flavanone 2-hydroxylase.

However, a comparison with the amino acid sequence of flavanone 2-hydroxylase encoded by CYP93B1 suggested that the cDNA of ANFNS1 is not a full-length cDNA, lacking the portion corresponding to approximately 65 amino acid residues from the initiating methionine. The ANFNS1 cDNA was therefore used as a probe for-rescreening of the snapdragon cDNA library, to obtain cDNA (ANFNS2) which was believed to include the full-length amino acid sequence. The protein encoded by ANFNS2 obtained here exhibited 53% identity on the amino acid level with flavanone 2-hydroxylase encoded by snapdragon CYP93B1. The nucleotide sequence of ANFNS2 is listed as SEQ.ID. No.1, and the amino acid sequence deduced therefrom is listed as SEQ.ID. No.2.

Example 2

Cloning of Torenia Flavone Synthase II Gene

RNA was extracted from approximately 2 g of buds of a torenia variety (variety name: Sunrenive, variety Registration Application No.: 7433 according to the Seeds and Seedlings Law, by Suntory Ltd.) and the polyA+ RNA was obtained with an Oligotex. The polyA+ RNA was used as a template to prepare a cDNA library using a Lambda ZAPII cDNA Library Synthesis Kit (Stratagene) by the method recommended by Stratagene as mentioned in Example 1. The cDNA library was screened using a mixture of the aforementioned CYP93B1 cDNA and ANFNS1 cDNA as the probes. The screening and detection of positive clones were carried out under the low stringent conditions as described in Example 1.

One positive clone was obtained, and was designated as TFNS5. Upon determining the full nucleotide sequence of TFNS5 cDNA, it was found that the protein encoded by TFNS5 cDNA exhibited 52% identity on the amino acid level with flavanone-2-hydroxylase encoded by snapdragon CYP93B1. This TFNS5 cDNA also had high identity of 77% with the protein encoded by ANFNS2, the snapdragon-derived cDNA obtained in Example 1. The determined nucleotide sequence is listed as SEQ.ID. No.3, and the amino acid sequence deduced therefrom is listed as SEQ.ID. No.4.

Example 3

Expression of Torenia Flavone Synthase II Gene in Yeast

The following experiment was conducted in order to detect the enzyme activity of the protein encoded by TFNS5, the torenia cDNA obtained in Example 2. Parts of the outside of the translated region of the gene were modified to introduce restriction enzyme sites therein to prepare a sense primer (5'-AAATA GGATCCAAGCatgGACACAGTCTTAA-3'; underline=BamHI site; lowercase letters: initiation codon) (SEQ.ID. No.5) and an antisense primer (5'-CCCT TCTAGATCAAGCACCCGATATTGTGGCCGGG-3'; underline=XbaI site; lowercase letters: termination codon) (SEQ.ID. No.6) were used with KOD polymerase (Toyobo) for PCR reaction. The PCR conditions were 98° C. for one minute, 20 cycles of (98° C. for 15 seconds, 55° C. for 10 seconds, 74° C. for 30 seconds), followed by 74° C. for 10 minutes.

After introducing the resultant PCR product into the EcoRV site of pBluescriptII SK(−) (Stratagene), it was digested with restriction enzymes BamHI and XbaI and introduced at the BamHI-XbaI sites of the yeast expression vector pYES2 (Invitrogen). The resultant plasmid was then introduced into BJ2168 yeast (Nihon Gene). The enzyme activity was measured by the method described by Akashi et al. (FEBS Lett., 431 (1998), Akashi et al., p. 287). The transformed yeast cells were cultured in 20 ml of selective medium (6.7 mg/mi amino acid-free yeast nitrogen base (Difco), 20 mg/ml glucose, 30 µg/ml leucine, 20 µg/ml tryptophan and 5 mg/ml casamino acid), at 30° C. for 24 hours.

After harvesting the yeast cells with centrifugation, the harvested yeast cells were cultured at 30° C. for 48 hours in an expressing medium (10 mg/ml yeast extract, 10 mg/ml peptone, 2 µg/ml hemin, 20 mg/ml galactose). After collecting the yeast cells, they were washed by suspending in water and collecting them. Glass beads were used for 10 minutes of disrupting, after which the cells were centrifuged at 8000×g for 10 minutes. The supernatant was further centrifuged at 15,000×g for 10 minutes to obtain a crude enzyme fraction.

A mixture of 15 µg of (R,S)-naringenin (dissolved in 30 µl of 2-methoxyethanol), 1 ml of crude enzyme solution and 1 mM NADPH (total reaction mixture volume: 1.05 ml) was reacted at 30° C. for 2 hours. After terminating the reaction by addition of 30 µl of acetic acid, 1 ml of ethyl acetate was added and mixed therewith. After centrifugation, the ethyl acetate layer was dried with an evaporator. The residue was dissolved in 100 µl of methanol and analyzed by HPLC. The analysis was carried out according to the method described by Akashi et al. The acid treatment involved dissolution of the evaporator-dried sample in 150 µl of ethanol containing 10% hydrochloric acid, and stirring for 30 minutes. This was diluted with 1.3 ml of water, 800 µl of ethyl acetate was further added and mixed therewith, and after centrifugation, the ethyl acetate layer was recovered. This was then dried, dissolved in 200 µl of methanol, and analyzed by HPLC.

The yeast expressing licorice CYP93B1 produced 2-hydroxynaringenin from naringenin, but yielded no apigenin (FIG. 1, A) only upon acid treatment of the reaction mixture, apigenin was yielded from 2-hydroxynaringenin (FIG. 1, B). In contrast, the yeast expressing torenia TFNS5 yielded apigenin from naringenin without acid treatment of the reaction mixture (FIG. 1, C). This demonstrated that TFNS5 encodes a flavone synthase II.

Example 4

Expression of Snapdragon Flavone Synthase II Gene in Yeast

An approximately 1400 bp DNA fragment obtained by digesting ANFNS2 cDNA with BamHI and SphI, an approximately 350 bp DNA fragment obtained by digesting the same with SphI and BamHI, and pYES2 digested with BamHI and XhoI were ligated to obtain a plasmid, which was then introduced into yeast by the same method as described in Example 3. The resultant recombinant yeast cells were used to measure the flavone synthesis activity by the same method as in Example 3. The yeast expressing the snapdragon-derived ANFNS2 produced apigenin without acid treatment, thus demonstrating that ANFNS2 encodes a flavone synthase II.

Example 5

Construction of Expression Vector in Plants

A plant expression vector was constructed to introduce TFNS5, the torenia cDNA obtained in Example 2, into plants. After digesting pBE2113-GUS (Plant Cell Physiol., 37 (1996), Mitsuhara et al., p. 49) with SacI, a blunting kit (Takara) was used to blunt the ends, after which a XhoI linker (Toyobo) was inserted. The resulting plasmid was then digested with HindIII and EcoRI, and an approximately-3 kb DNA fragment was recovered. The DNA fragment was linked to the HindIII/EcoRI site of the binary vector pBINPLUS to,prepare pBE2113'. Vector PBINPLUS used here was obtained by modifying the binary vector Bin19 (Nucl. Acids Res., 12 (1984), Bevan, p. 8711), which is widely used for gene introduction into plants using Agrobacterium cells, in the manner reported by van Engelen et al. (Transgenic Research, 4 (1995), van Engelen et al., p. 288).

The TFNS5 cDNA was cut out of SK(−) vector by cleavage with BamHI/XhoI, and an approximately 1.7 kb fragment thus obtained was ligated to the BamHI/XhoI sites of the aforementioned binary vector pBE2113'. The construct thus obtained, pSPB441, expresses TFNS5 cDNA in the sense direction under the control of 35S cauliflower mosaic virus promoter having a double repeat of the enhancer sequence (Plant cell Physiol., 37 (1996), Mitsuhara et al., p. 49).

Example 6

Alteration of Torenia Flower Color

A torenia variety (variety name: Sunrenive, Variety Registration Application No.: 7433 according to the Seeds and Seedlings Law, by Suntory Ltd.) was transformed with pSPB441 constructed in Example 5 above, according to the method of Aida et al. (Breeding Science, 45 (1995), Aida et al., p. 71). Over 95% of the obtained transformants showed alteration of the flower color from the dark purple of the parent strain to a light purple. The left and the right flower petal colors of four flower petals were measured. While the flower petal color of the parent strain was Number 89A according to the Royal Horticultural Society Color Chart, the typical flower petal colors of the transformants were 82C, 87D, 87C, 88D, 91A, etc. These results indicated that introduction of TFNS5 into plants can alter flower colors.

In the transformed individuals, the amount of flavones ranged ⅕ to ⅒ that of the host, while the amount of anthocyanins was reduced to about ⅓ that of the host. Also detected were flavanones (naringenin, eriodictyol and pentahydroxyflavanone) which are flavone biosynthesis precursors that were not detected in the host.

Example 7

Expression of Flavone Synthase in Petunias

Plasmid pSPB441 was introduced into a petunia variety (variety name: Revolution Violet Mini, Variety Registration Application No.: 9217, according to the Seeds and Seedlings Law, by Suntory Ltd.) according to the method of Napoli et.al. (Plant Cell, 2, (1990), Napoli et al., p. 279). Changes in flower colors occurred in two of the resultant transformants, where the flower colors were lighter than the parent strain. The flower color of the parent strain was Number 88A according to the Royal Horticultural Society Color Chart, whereas 87A in the transformants. Also, while no flavones were detected in the parent strain, a flavone, luteolin, was detected in the transformed strains.

Example 8

Cloning of Perilla Flavone Synthase II Gene

The method described in Example 1 was used to screen a cDNA library prepared from leaves of red perilla (*Perilla frutescens*) according to the method of Gong et al. (Plant Mol. Biol., 35, (1997), Gong et al., p. 915) using λgt10 (Stratagene) as the vector. Culturing, DNA preparation and subcloning of the resulting phage clones #3 were carried out according to the method of Gong et al. (Plant Mol. Biol., 35, (1997), Gong et al., p. 915), and the nucleotide sequence was determined and listed as SEQ.ID. No.7. The deduced amino acid sequence encoded by this nucleotide sequence was listed as SEQ.ID. No.8. This amino acid sequence showed 76% and 75% identity with TFNS5 and ANFNS2, respectively. It also showed 52% identity with CYP93B1.

Example 9

Expression of Perilla Flavone Synthase II Gene in Yeast

The phage clone #3 obtained in Example 8 was used as a template for PCR by the method described in Example 3, using Lambda Arm Primer (Stratagene). The amplified DNA fragment was subcloned at the EcoRV site of pBluescript KS(-). A clone with the initiation codon of perilla flavone synthase II cDNA on the SalI site side of pBluescript KS(-) was selected, and was designated as pFS3. The nucleotide sequence of the cDNA insert of pFS3 was determined, and PCR was conducted to confirm the absence of errors.

An approximately 1.8 kb DNA fragment obtained by digesting pFS3 with SalI and XbaI was ligated with pYES2 digested with XhoI and XbaI (Example 3) to obtain a plasmid which was designated as pYFS3, and this was introduced into yeast BJ2168 by the method described in Example 3. When the flavone synthase activity of this recombinant yeast was measured by the method described in Example 3, production of apigenin from naringenin was confirmed, indicating that the perilla phage clone #3 cDNA encodes a protein with flavone synthase II activity.

INDUSTRIAL APPLICABILITY

It is possible to alter flower colors by linking cDNA of the invention to an appropriate plant expression vector and introducing it into plants to express or inhibit expression of flavone synthases. Furthermore, by expressing the flavone synthase genes not only in petals but also in entire plants or their appropriate organs, it is possible to increase the resistance agasint microorganisms of plants or to improve the nitrogen fixing ability of legumes by promoting association with rhizosphere microorganisms, as well as to improve the protective effects of plants against ultraviolet rays and light.

---

The invention claimed is:

1. An isolated DNA or RNA encoding a protein, wherein said protein has an activity of synthesizing flavones from flavanones, further wherein the protein has the amino acid sequence as shown in SEQ ID NO: 2.

2. An isolated DNA having the nucleotide sequence of SEQ ID NO: 1.

3. A vector comprising the isolated gene DNA according to claim 1.

4. A plant host transformed by the vector according to claim 3.

5. A method of producing a protein with flavone-synthesizing activity, comprising culturing or growing a plant host according to claim 4, and recovering said protein from said plant host.

6. A plant, a progeny thereof, or a tissue thereof, wherein said plant, progeny or tissue comprises the isolated DNA or RNA of claim 1.

7. A cut flower from the plant or the progeny thereof according to claim 6 comprising said isolated DNA or RNA.

8. A method of altering a composition of flavonoids or amount thereof, or both the composition and amount in a plant host comprising:
introducing a vector having the DNA according to claim 1 into a plant host;
culturing or growing said plant host; and
recovering said flavones;
wherein said flavones are included in a composition of flavonoids.

9. The method according to claim 8, wherein said DNA is inserted in the vector.

10. A method of altering the amount of a flavone in a plant host comprising:
introducing a vector having the DNA according to claim 1 into a plant host;
culturing or growing said host, wherein said flavone synthase gene is expressed and amount of flavone altered.

11. A method of altering the color of a flower comprising:
introducing a vector having the DNA according to claim 1 into a flower plant;
culturing or growing said flower plant, wherein said DNA is expressed and expression of said DNA alters the flower color in said flower plant.

12. A method of bluing the color of a flower comprising:
introducing a vector having the DNA according to claim 1 into a flower plant; and
culturing or growing said flower plant, wherein the DNA is expressed and flavone is produced in the flower plant.

13. A method of reddening the color of a flower comprising:
introducing a vector having the DNA according to claim 1 into a flower plant; and
culturing or growing said flower plant, wherein expression of the DNA is suppressed in the flower plant.

14. A method of altering the photosensitivity of a plant comprising:
introducing a vector having the DNA according to claim 1 into a plant; and
culturing or growing said plant, wherein the DNA is expressed.

15. A method of controlling the interaction between a plant and microorganisms comprising:
introducing a vector having the DNA according to claim 1 into a plant; and
culturing or growing said plant, wherein the DNA is expressed and flavone produced in the plant.

16. A method of altering a composition of flavones or amount thereof, or both the composition and amount in a plant or tissue thereof comprising:
introducing a vector having the DNA according to claim 1 into a plant or tissue thereof; and
culturing or growing said plant or tissue, whereby the DNA is expressed in said plant or tissue.

17. A method of suppressing flavone synthesis in a plant or tissue thereof, comprising:
introducing a vector having the DNA according to claim 1 into a plant or tissue thereof; and
culturing or growing said plant or tissue, whereby expression of the DNA is suppressed in said plant.

18. A method of increasing an amount of flavone in a flower petal, comprising:
introducing a vector having the DNA according to claim 1 into a plant or tissue thereof; and
culturing or growing said plant or tissue, whereby the DNA is expressed in said plant.

19. A method of decreasing an amount of flavone in a flower petal, comprising:
introducing a vector having the DNA according to claim 1 into a plant or tissue thereof; and
culturing or growing said plant or tissue, whereby expression of the DNA is suppressed in said plant.

20. A method of synthesizing a flavone from flavanone comprising:
introducing a vector having the DNA according to claim 1 into a plant host having flavanones;
culturing or growing said plant host, whereby said DNA is expressed in said plant host to produce a flavone synthase; and
said flavone synthase synthesizes flavone from said flavanone.

21. A method for producing a flavone synthase comprising:
introducing a vector having the DNA according to claim 1 into a plant host; and
culturing or growing said plant host, whereby said DNA is expressed in said plant host to produce a flavone synthase.

* * * * *